(12) United States Patent
Nierlich et al.

(10) Patent No.: US 7,462,745 B2
(45) Date of Patent: Dec. 9, 2008

(54) METHOD FOR THE PRODUCTION OF 2,7-OCTADIENYL DERIVATIVES

(75) Inventors: Franz Nierlich, Marl (DE); Cornelia Borgmann, Frankfurt (DE); Dirk Roettger, Recklinghausen (DE); Stephan Houbrechts, Duffel (BE); Dietrich Maschmeyer, Recklinghausen (DE)

(73) Assignee: OXENO Olefinchemie GmbH, Marl (DE)

( * ) Notice: Subject to any disclaimer, the term of this patent is extended or adjusted under 35 U.S.C. 154(b) by 82 days.

(21) Appl. No.: 11/574,063

(22) PCT Filed: Aug. 23, 2005

(86) PCT No.: PCT/EP2005/054135

§ 371 (c)(1),
(2), (4) Date: Feb. 22, 2007

(87) PCT Pub. No.: WO2006/024614

PCT Pub. Date: Mar. 9, 2006

(65) Prior Publication Data

US 2008/0021234 A1 Jan. 24, 2008

(30) Foreign Application Priority Data

Aug. 28, 2004 (DE) .......... 10 2004 041 778
Aug. 1, 2005 (DE) .......... 10 2005 036 039

(51) Int. Cl.
*C07C 209/60* (2006.01)
*C07C 67/04* (2006.01)
*C07C 29/36* (2006.01)
*C07C 41/06* (2006.01)

(52) U.S. Cl. .......... 564/485; 568/398; 568/408

(58) Field of Classification Search .......... None
See application file for complete search history.

(56) References Cited

U.S. PATENT DOCUMENTS

| | | | |
|---|---|---|---|
| 5,177,282 | A | 1/1993 | Nierlich et al. |
| 5,712,403 | A * | 1/1998 | Sato et al. .......... 556/19 |
| 6,015,928 | A | 1/2000 | Gubisch et al. |
| 6,184,424 | B1 | 2/2001 | Bueschken et al. |
| 6,239,318 | B1 | 5/2001 | Schuler et al. |
| 6,331,657 | B1 | 12/2001 | Kaizik et al. |
| 6,403,836 | B2 | 6/2002 | Kaizik et al. |
| 6,407,295 | B1 | 6/2002 | Kaizik et al. |
| 6,482,992 | B2 | 11/2002 | Scholz et al. |
| 6,492,564 | B1 | 12/2002 | Wiese et al. |
| 6,500,991 | B2 | 12/2002 | Wiese et al. |
| 6,555,716 | B2 | 4/2003 | Protzmann et al. |
| 6,570,033 | B2 | 5/2003 | Rottger et al. |
| 6,627,782 | B2 | 9/2003 | Kaizik et al. |
| 6,680,414 | B2 | 1/2004 | Knoop et al. |
| 6,720,457 | B2 | 4/2004 | Drees et al. |
| 6,818,770 | B2 | 11/2004 | Selent et al. |
| 6,924,389 | B2 | 8/2005 | Jackstell et al. |
| 6,956,133 | B2 | 10/2005 | Jackstell et al. |
| 6,960,699 | B2 | 11/2005 | Totsch et al. |
| 7,002,053 | B2 | 2/2006 | Nierlich et al. |
| 7,009,068 | B2 | 3/2006 | Schmutzler et al. |
| 7,026,523 | B2 | 4/2006 | Roettger et al. |
| 7,030,286 | B2 | 4/2006 | Roettger et al. |
| 7,109,346 | B2 | 9/2006 | Beller et al. |
| 7,115,790 | B2 | 10/2006 | Beller et al. |
| 7,138,552 | B2 | 11/2006 | Kaizik et al. |
| 7,154,012 | B2 | 12/2006 | Lueken et al. |
| 7,161,020 | B2 | 1/2007 | Selent et al. |
| 7,161,053 | B2 | 1/2007 | Beckmann et al. |
| 7,179,947 | B2 | 2/2007 | Lueken et al. |
| 7,193,116 | B2 | 3/2007 | Moeller et al. |
| 7,217,828 | B2 | 5/2007 | Selent et al. |
| 7,232,931 | B2 | 6/2007 | Toetsch et al. |
| 2004/0238787 | A1 | 12/2004 | Wiese et al. |
| 2004/0242947 | A1 | 12/2004 | Beller et al. |
| 2005/0240039 | A1 | 10/2005 | Rottger et al. |
| 2005/0256281 | A1 | 11/2005 | Grund et al. |
| 2006/0036121 | A1 | 2/2006 | Kaizik et al. |
| 2006/0161017 | A1 | 7/2006 | Grass et al. |
| 2006/0183936 | A1 | 8/2006 | Grass et al. |
| 2006/0241324 | A1 | 10/2006 | Moeller et al. |
| 2006/0281959 | A1 | 12/2006 | Krissmann et al. |
| 2007/0027346 | A1 | 2/2007 | Kaizik et al. |
| 2007/0043245 | A1 | 2/2007 | Kaizik et al. |
| 2007/0112219 | A1 | 5/2007 | Ortmann et al. |
| 2007/0117995 | A1 | 5/2007 | Ortmann et al. |
| 2008/0021234 | A1 | 1/2008 | Nierlich et al. |

FOREIGN PATENT DOCUMENTS

| | | |
|---|---|---|
| DE | 103 12 829 | 1/2004 |
| GB | 1066765 | 4/1967 |
| WO | 91 09822 | 7/1991 |
| WO | 98 12160 | 3/1998 |

OTHER PUBLICATIONS

U.S. Appl. No. 10/588,762, filed Jan. 10, 2007, Wiese et al.

(Continued)

*Primary Examiner*—Brian J Davis
(74) *Attorney, Agent, or Firm*—Oblon, Spivak, McClelland, Maier & Neustadt, P.C.

(57) ABSTRACT

Process for preparing 1-octa-2,7-dienyl derivatives by reacting a 1,3-butadiene-containing hydrocarbon mixture, in particular a $C_4$ fraction from a cracker, with nucleophiles, in which acetylenically unsaturated compounds are removed from the starting hydrocarbon mixture by selective hydrogenation and a telomerization is subsequently carried out.

19 Claims, No Drawings

OTHER PUBLICATIONS

U.S. Appl. No. 11/721,978, filed Jun. 16, 2007, Beller et al.
U.S. Appl. No. 11/574,063, filed Feb. 22, 2007, Neirlich et al.
U.S. Appl. No. 11/574,060, filed Feb. 22, 2007, Borgmann et al.
U.S. Appl. No. 11/574,018, filed Feb. 21, 2007, Borgmann et al.
U.S. Appl. No. 11/574,063, filed Feb. 22, 2007, Nierlich et al.
U.S. Appl. No. 12/065,091, filed Feb. 28, 2008, Hess et al.
U.S. Appl. No. 12/088,041, filed Mar. 25, 2008, Weise et al.

* cited by examiner

METHOD FOR THE PRODUCTION OF 2,7-OCTADIENYL DERIVATIVES

The invention relates to a process for preparing 1-octa-2,7-dienyl derivatives by reacting a 1,3t-butadiene-containing hydrocarbon mixture, in particular a $C_4$ fraction from a cracker, with nucleophiles.

The telomerization products (unsaturated amines, unsaturated alcohols and esters and ethers thereof) formed from two mol of 1,3-butadiene and one mol of nucleophile in this reaction are starting materials for organic syntheses. The oxygen-containing derivatives are precursors for the preparation of linear $C_8$-alcohols and $C_8$-olefins, in particular 1-octanol and 1-octene. 1-Octanol is in turn used, for example, for producing plasticizers. 1-Octene is a valuable comonomer for the modification of polyethylene and polypropylene.

The telomerization of butadiene with a nucleophile to form octadienyl derivatives is catalyzed by metal complexes, in particular palladium compounds.

Examples of telomerization reactions are described, inter alia, in E. J. Smutny, J. Am. Chem. Soc. 1967, 89, 6793; S. Takahashi, T. Shibano, N. Hagihara, Tetrahedron Lett. 1967, 2451, EP-A0 561 779. U.S. Pat. Nos. 3,499,042, 3,530,187, GB 1 178 812, NL 6 816 008, GB 1 248 593, U.S. Pat. Nos. 3,670,029, 3,670,032, 3,769,352, 3,887,627, GB 1,354,507, DE 20 40 708, U.S. Pat. Nos. 4,142,060, 4,146,738, 4,196,135, GB 1 535 718, U.S. Pat. No. 4,104,471, DE 21 61 750 and EP-A-0 218 100.

As starting materials for the preparation of octadienyl derivatives, it is possible to use pure 1,3-butadiene or 1,3-butadiene-containing hydrocarbon mixtures such as the $C_4$ fraction from a cracker.

Owing to the difficulty of separating it from other components, 1,3-butadiene is a relatively expensive starting material. It is therefore usually more economical to choose 1,3-butadiene-containing hydrocarbon mixtures as starting materials for the telomerization. This is possible since most accompanying substances for example saturated hydrocarbons such as n-butane or isobutane or monoolefins such as isobutene and linear butenes, are inert in the telomerization reaction. Only inhibitors, i.e. substances which reduce the space-time yield or the selectivity or increase the catalyst consumption, have to be separated off.

According to DE 195 23 335, it is advisable when using the $C_4$ fraction from naphtha crackers as 1,3-butadiene-containing raw material to limit the concentration of acetylenic compounds and of allenes in the starting material for the telomerization. The sum of acetylenically and allenically unsaturated compounds should not exceed 1% by mass based on 1,3-butadiene. To remove these interfering components, reference is made to known methods, without particular methods being described or cited.

With reference to this patent specification (DE 195 23 335), DE 101 49 348, DE 102 29 290 and DE 103 29 042 state that it is advantageous to remove acetylenic and allenic compounds prior to the telomerization, without indicating concentration limits.

WO 91-09822 states that it is advantageous to remove acetylenically unsaturated compounds, if these are present, from the $C_4$ mixture obtained from cracking of naphtha, gas oil or LPG by selective hydrogenation prior to the telomerization. The hydrogenation process used here is not disclosed. In the examples, a raw material which has a total content of acetylenes of less than 60 ppm and contains no detectable amount of allenes.

The acetylenic compounds can be separated off by extraction or hydrogenation of these compounds. When the acetylenic compounds (methylacetylene (propyne), ethylacetylene (butyne), vinylacetylene (butenine)) are removed by hydrogenation, use is made of processes in which the acetylenic compounds are hydrogenated highly selectively essentially without hydrogenation of 1,3-butadiene and monoolefins. As catalysts, use is made of hydrogenation catalysts such as copper, copper in combination with base metals, copper in combination with noble metals or metal catalysts comprising metals of transition group VIII of the Periodic Table of the Elements, for example palladium catalysts. Appropriate processes are described, inter alia, in the following patent specifications: U.S. Pat. Nos. 6,576,588, 6,417,419, 6,225,515, 6,015,933, 6,194,626, 6,040,489, 4,493,906, 4,440,956, 4,101,451, 3,912,789, 3,751,508, 3,541,178, 3,327,013, 3,218,268, EP 1 217 060, EP 1 151 790, EP 1 070 695, EP 0 273 900, NL 6 613 942.

The selective removal of allenes, in particular 1,2-butadiene, by hydrogenation is significantly more difficult than the selective removal of acetylenic compounds. The reactivity of 1,2-butadiene in the hydrogenation is only slightly higher than that of 1,3-butadiene. For this reason, 1,3-butadiene losses are unavoidable in the removal of 1,2-butadiene from 1,3-butadiene-containing hydrocarbon mixtures by hydrogenation.

For example, WO 98/12160 discloses a process for the simultaneous removal of acetylenic compounds and 1,2-butadiene from a 1,3-butadiene-containing hydrocarbon stream by hydrogenation over a palladium catalyst in a reactive distillation column. Although the content of acetylenic compounds in the overhead product has been reduced by only about 60% and that of 1,2-butadiene has been reduced by only about 32% in example 1 described there, 3% of the 1,3-butadiene had been lost as a result of hydrogenation.

In the preparation of 2,7-octadienyl derivatives from a $C_4$ fraction from a cracker, either part of the 1,3-butadiene is lost in the removal of inhibitors (and)/or a lower space-time yield or selectivity is obtained in the telomerization or the catalyst consumption is higher due to the inhibitors.

It is therefore an object of the invention to develop a process which starts out from a $C_4$ fraction from a cracker and gives a high yield of 2,7-octadienyl derivatives based on 1,3-butadiene in the $C_4$ fraction from a cracker and/or has a low consumption of telomerization catalyst.

It has now surprisingly been found that acetylenically unsaturated compounds act as inhibitors in the telomerization of 1,3-butadiene to form 2,7-octadienyl derivatives, but allenically unsaturated compounds (for example 1,2-butadiene) do not act as inhibitors. This was not to be expected, since it is stated in the prior art, e.g. DE 195 23 335 that the concentration of allenes (e.g. 1,2-butadiene) should be reduced if possible.

The invention accordingly provides a process for preparing a compound of the formula I

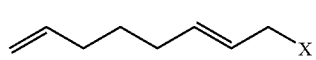

in which X is an $OR^{1a}$ or $NR^{1a}R^{1b}$ radical where $R^{1a}$ and $R^{1b}$ are each hydrogen, a substituted or unsubstituted alkyl, aryl or acyl radical, from a 1,3-butadiene-containing hydrocarbon stream comprising allenically unsaturated compounds and also more than 100 ppm by mass of acetylenically unsaturated compounds, in which process the acetylenically unsaturated compounds are removed in a first process step and 1,3-butadiene is reacted with a compound containing active hydrogen or with a nucleophile (telogen) in the presence of a metal compound in a second process step (telomerization step) wherein the hydrocarbon stream which is obtained from the first process step and is used as starting material in the second process step has a content of acetylenically unsaturated compounds of less than or equal to 100 ppm by mass and a content of allenically unsaturated compounds which is at least 75% (relative) of the original content of allenically unsaturated compounds.

The compound of the formula I can be present both in the cis for and in the trans form.

As a result of a removal of the allenes being omitted in the first process step, less 1,3-butadiene is unintentionally hydrogenated or partially hydrogenated in the first process step, so that yield losses based on the 1,3-butadiene content in the hydrocarbon feed stream can be minimized.

The process of the invention also has the advantage that the allenes or cumulenes, i.e. compounds having cumulated double bonds, e.g. 1,2-butadiene, which are important starting materials for organic synthesis are not destroyed in the two process steps but remain in the hydrocarbon stream and can be separated off after the second process step, viz. the telomerization, in the work-up of the telomerization product.

The process of the invention is described by way of example below without the invention, whose scope is defined by the claims and the description, being restricted thereby. The claims themselves are also part of the disclosure of the present invention.

The process of the invention for preparing a compound of the formula I

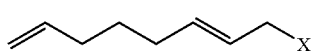

I in which X is an $OR^{1a}$ or $NR^{1a}R^{1b}$ radical, where $R^{1a}$ and $R^{1b}$ are selected independently from among hydrogen, a linear. branched or cyclic $C_1$-$C_{22}$-alkyl group, an alkenyl group, an alkynyl group, a $C_5$-$C_{18}$-aryl group or a —CO-alkyl-($C_1$-$C_8$) group or a —CO-aryl-($C_5$-$C_{10}$) group, with these groups being able to contain substituents selected from the group consisting of —CN, —COOH, —COO-alkyl-($C_1$-$C_8$), —CO-alkyl-($C_1$-$C_8$), -aryl-($C_5$-$C_{10}$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$, —NO$_2$ and the radicals $R^{1a}$ and $R^{1b}$ being able to be joined to one another via covalent bonds, from a 1,3t-butadiene-containing hydrocarbon stream comprising allenically unsaturated compounds and more than 100 ppm by mass of acetylenically unsaturated compounds, in which process the acetylenically unsaturated compounds are removed in a first process step and 1,3-butadiene is reacted with a nucleophile (a compound containing active hydrogen, namely the telogen) in the presence of a metal compound in a second process step (telomerization step), is distinguished by the hydrocarbon stream which is obtained from the first process step and is used as starting material in the second process step having a content of acetylenically unsaturated compounds of less than or equal to 100 ppm by mass and a content of allenically unsaturated compounds which is at least 75% (relative) of the original content of allenically unsaturated compounds.

The process of the invention enables, in particular, compounds of the formula IIa or IIb,

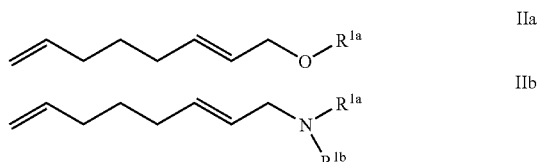

to be prepared by reacting 1,3-butadiene with a nucleophile of the formula III, IV or V

$R^{1a}$—O—H (III)

$(R^{1a})(R^{1b})N$—H (IV)

$R^{1a}$—COOH (V)

where $R^{1a}$ and $R^{1b}$ are as defined above.

The process of the invention is particularly preferably used for preparing compounds of the formula I in which X is $OR^{1a}$ or $NR^{1a}R^{1b}$, where $R^{1a}$ is H, methyl, ethyl, n-propyl, isopropyl, tert-butyl, n-butyl, sec-butyl, pentyl, hexyl, heptyl, octyl, octenyl, octadienyl, isononyl, 2-ethylhexyl n-nonyl, phenyl, m-, o- or p-methylphenyl, naphthyl, 2,4-di-tert-butylphenyl, 2,6-di-tert-butylmethylphenyl, hydrogencarbonyl, methyl-carbonyl, ethylcarbonyl, propylcarbonyl or phenylcarbonyl and/or $R^{1b}$ is H, methyl, ethyl, n-propyl isopropyl, tert-butyl, n-butyl, sec-butyl, pentyl, hexyl, heptyl, octyl, octenyl, octadienyl, isononyl, 2-ethylhexyl, n-nonyl, phenyl, m-, o- or p-methylphenyl, naphthyl, 2,4-di-tert-butylphenyl, 2,6-di-tert-butylmethylphenyl, hydrogencarbonyl, methylcarbonyl, ethylcarbonyl, propylcarbonyl or phenylcarbonyl. The process of the invention is particularly preferably used for preparing a compound of the formula IIa in which $R^{1a}$=hydrogen, methyl, ethyl, phenyl or methylcarbonyl. The compounds of the formulae IIa and IIb can be present both in the cis form and in the trans form.

Starting materials for the process of the invention are 1,3-butadiene-rich hydrocarbon streams comprising, inter alia, allenically unsaturated compounds and more than 100 ppm by mass of acetylenically unsaturated compounds. As hydrocarbon stream, it is possible to use, in particular, a $C_4$-hydrocarbon fraction. The hydrocarbon streams can preferably be, for example, mixtures of 1,3-butadiene with other $C_4$- and $C_3$- or $C_5$-hydrocarbons. Such mixtures are obtained, for example, in cracking processes for the production of ethylene and propylene, in which refinery gases, naphtha, gas oil, LPG (liquefied petroleum gas), NGL (natural gas liquid), etc., are reacted. The $C_4$ fractions obtained as by-product in the processes can comprise 1,3-butadiene together with monoolefins (1-butene, cis-2-butene, trans-2-butene, isobutene), saturated hydrocarbons (n-butane, isobutane), acetylenically unsaturated compounds (ethylacetylene (butyne), vinylacetylene (butenine), methylacetylene (propyne)) and also allenically unsaturated compounds (mainly 1,2-butadiene). These fractions can further comprise small amounts of $C_3$- and $C_5$-hydrocarbons. The composition of the $C_4$ fractions is dependent on the particular cracking process, the operating parameters and the feed. The concentrations of the individual components are typically in the following ranges:

| Component | % by mass |
| --- | --- |
| 1,3-Butadiene | 25-70 |
| 1-Butene | 9-25 |
| 2-Butenes | 4-20 |
| Isobutene | 10-35 |
| n-Butane | 0.5-8 |
| Isobutane | 0.5-6 |
| Σ acetylenic compounds | 0.05-4 |
| 1,2-Butadiene | 0.05-2 |

In the process of the invention, preference is given to using hydrocarbon mixtures having a 1,3-butadiene content of greater than 35% by mass.

The starting hydrocarbons can frequently contain traces of oxygen compounds, nitrogen compounds, sulfur compounds, halogen compounds, in particular chlorine compounds, and heavy metal compounds which could interfere in the process of the invention. It is therefore advantageous to separate off these compounds first. Interfering impurities can be, for examples stabilizers such as tert-butylcatechol (TBC) or carbon dioxide or carbonyls such as acetone or acetaldehyde.

These impurities can be separated off by, for example, scrubbing, in particular with water or aqueous solutions, or by means of adsorbents.

A water scrub can completely or partly remove hydrophilic components, for example nitrogen components, from the hydrocarbon mixture. Examples of nitrogen components are acetonitrile and N-methylpyrrolidone (NMP). Oxygen compounds, too, can be partly removed by means of a water scrub. The water scrub can be carried out directly using water or else using aqueous solutions which can comprise salts such as $NaHSO_3$ (U.S. Pat. Nos. 3,682,779, 3,308,201, 4,125,568, 3,336,414 or 5,122,236).

It can be advantageous for the hydrocarbon mixture to go through a drying step after the water scrub. Drying can be carried out by the methods known from the prior art. If dissolved water is present, drying can, for example, be carried out using molecular sieves as desiccants or by azeotropic distillation. Free water can be separated off by phase separation, e.g. using a coalescer.

Adsorbents can be used to remove impurities present in the trace range. This can be advantageous because, for example, noble metal catalysts which react to traces of impurities with a significant decrease in activity are used in the second process step. Nitrogen compounds or sulfur compounds and also TBC are often removed by means of upstream adsorbents. Examples of adsorbents are aluminum oxides, molecular sieves, zeolites, activated carbon or metal-impregnated aluminas (e.g. U.S. Pat. No. 4,571,445 or WO 02/53685). Adsorbents are marketed by various companies, for example by Alcoa under the name Selexsorb®, by UOP or by Axens, e.g the product series SAS, MS, AA, TG, TGS or CMG.

In a first step of the process of the invention, the acetylenically unsaturated compounds are separated off or removed from the hydrocarbon stream, which can have been purified first, to a content of less than or equal to 100 ppm by mass, preferably less than or equal to 50 ppm by mass and particularly preferably less than or equal to 20 ppm by mass, before the hydrocarbon stream is used in the telomerization step. The separation/removal can be carried out, for example, by extraction or hydrogenation of the acetylenically unsaturated compounds. Any methylacetylene present can also be removed by distillation.

The removal of acetylenic compounds by extraction has been known for a long time and is, as work-up step, an integral part of most plants which recover 1,3-butadiene from $C_4$ fractions from a cracker. A process for the extractive removal of acetylenically unsaturated compounds from a $C_4$ fraction from a cracker is described, for example, in *Erdöl und Kohle-Erdgas-Petrochemie vereinigt mif Brennstoffchemie* vol. 34, number 8, Aug. 1981, pages 343-346. In this process, the multiply unsaturated hydrocarbons and also the acetylenically unsaturated compounds are separated off from the monoolefins and saturated hydrocarbons by extractive distillation with water-containing NMP in a first step. The unsaturated hydrocarbons are separated off from the NMP extract by distillation and the acetylenically unsaturated compounds having 4 carbon atoms are separated off from the hydrocarbon distillate by means of a second extractive distillation with water-containing NMP. In the work-up of a $C_4$ fraction from a cracker, pure 1,3-butadiene is separated off by means of two further distillations, with methylacetylene and 1,2-butadiene being obtained as by-products. In the process of the invention, the multistage process described here can be carried out in the same way as a first process step, with the removal of 1,2-butadiene by distillation being dispensed with.

The removal of acetylenic compounds from a 1,3-butadiene-containing stream can optionally be carried out using one or more ionic liquid(s), e.g. as extractant.

The 1,3-butadiene-containing hydrocarbon streams which are obtained by extraction in this first process step and further comprise 1,2-butadiene and less than 100 ppm by mass of acetylenic compounds can be used as starting material in the second process step, either directly or after a work-up, preferably directly.

The removal of the acetylenically unsaturated compounds from the hydrocarbon stream used is preferably carried out by hydrogenation of the acetylenically unsaturated compounds. To avoid yield losses, especially of 1,3-butadiene and 1,2-butadiene, the hydrogenation process has to be very selective, i.e. the hydrogenation of 1,3- or 1,2-butadiene to linear butenes and the hydrogenation of butenes to butanes have to be very largely avoided. For the selective hydrogenation of acetylenic compounds in the presence of dienes and monoolefins, it is possible to use, for example, copper-containing catalysts. It is likewise possible to use catalysts comprising a noble metal of transition group VIII of the Periodic Table of the Elements, in particular palladium, or mixed catalysts. Particular preference is given to using copper-containing catalysts or catalysts comprising both palladium and copper.

The selective hydrogenation process can have one or more stages. When the hydrogenation is carried out in a plurality of stages or in a plurality of reactors connected in series, different catalysts can be used in the reactors (EP 0 273 900), A further suitable two-stage hydrogenation process is described in U.S. Pat. No. 4,277,313, in which the selective hydrogenation of a stream comprising acetylenically unsaturated compounds is followed by a subsequent extractive distillation to separate off 1,3-butadiene.

The catalyst activity and selectivity can also be influenced by addition of suitable solvents as are used. for example, in U.S. Pat. Nos. 4,587,369, 6,194,626 and 6,271,428. Furthermore, the hydrogenation can also be carried out in a reactive distillation or a distillation with an external reactor. In general, the hydrogenation can be carried out in the liquid phase or in the gas phase.

The selective hydrogenation as first process step is preferably carried out at a pressure of from 0.1 to 7 MPa, more preferably from 0.3 to 5 MPa. The temperature is preferably from 20 to 250° C., more preferably from 20 to 150° C. and particularly preferably from 30 to 80° C. (e.g. U.S. Pat. Nos. 4,440,956, 4,126,645 and 6,417,419). When the hydrogenation is carried out in the liquid phase, it is important to ensure that the hydrogen is fully dissolved, so that the occurrence of hot spots and thus unselective hydrogenation are avoided as far as possible (U.S. Pat. No. 3,912,789).

In a preferred embodiment of the first process step, the hydrogenation is carried out in the liquid phase over a copper-containing catalyst. A hydrogenation process which can be carried out as first process step is described, for example, in U.S. Pat. Nos. 3,912,789 and 6,417,419. More precise details regarding the catalyst and the process conditions under which the selective hydrogenation can be carried out may be found in U.S. Pat. No. 3,912,789, which is hereby expressly incorporated by reference. When this process is used as first process step of the process of the invention, the product from the first process step can, depending on the composition of the hydrocarbon feed mixture, have a higher content of allenically unsaturated compounds than the starting material. Carrying out the first process step as described in U.S. Pat. No. 3,912,789 thus has the advantage that allenically unsaturated compounds, in particular 1,2-butadiene, are not only not removed in the hydrogenation but the content of these compounds can even be increased in the product stream, depending on the composition of the original hydrocarbon stream.

The first process step of the process of the invention is therefore preferably carried out in the presence of a catalyst which comprises essentially a mixture of finely divided, metallic copper and a small amount of a polyvalent activator metal supported on gamma-aluminum oxide having a surface area of more than 10 m$^2$/g and containing from 0.1 to 1.5% by mass of $Na_2O$. Activator metals which can be present in the catalysts are, for example, silver, platinum, palladium, manganese, nickel, cobalt, chromium and/or molybdenum. If the activity of the catalysts drops, they can be regenerated in a simple fashion as described in U.S. Pat. No. 3,912,789, e.g. by firstly bringing the catalyst into contact with an oxygen-containing gas (burning off) and subsequently reducing the oxidized catalyst by means of hydrogen. The first process step preferably has two hydrogenation reactors, so that operation of the overall process can be continued during regeneration of a catalyst.

The first process step itself can, for example, be carried out by placing the catalyst in a reaction zone of a reactor through which the hydrocarbon stream is then passed. The reaction can be carried out at temperatures of from 10 to 150° C., preferably from 50 to 100° C. The reaction can be carried out at any pressure, but preference is given to selecting a pressure at which the process stream is present as a homogeneous liquid phase. The first process step will normally be carried out at superatmospheric pressure. The reaction is preferably carried out at a pressure of from 1.013 to 2.026 MPa.

Hydrocarbon streams which comprise olefinically unsaturated compounds and comprise up to a number of percent by volume of acetylenically unsaturated compounds can be hydrogenated selectively in this embodiment of the first process step according to the invention. Particularly good results are achieved when not more than 0.2% by volume of acetylenically unsaturated compounds are present in the hydrocarbon stream. Under such conditions, the hydrocarbon stream can be passed through the catalyst bed at a flow rate of from 1 to 5 $1*(1*h)^{-1}$, based on the volume of the catalyst bed. Further details can once again be found in U.S. Pat. No. 3,912,789.

The molar ratio of hydrogen to acetylenic bonds is preferably at least 1. The first process step is particularly preferably carried out using a molar excess of hydrogen. The first process step of the process of the invention is preferably carried out at a molar ratio of hydrogen to acetylenically unsaturated bonds of from 1 to 2.

The first process step of the selective hydrogenation can, for example, also be carried out as described in U.S. Pat. No. 6,417,419. In this process, too, a copper-containing catalyst is used. In this embodiment of the first process step according to the invention, the selective hydrogenation is preferably carried out at a temperature of from 20 to 80° C., preferably at a pressure of from 1.5 to 5.0 MPa and an LHSV in the range from 0.5 to 10. The selective hydrogenation is preferably carried out with addition of such an amount of hydrogen that the ratio of hydrogen to acetylenes is from 1 to 5.

A further process for the selective hydrogenation of acetylenically unsaturated compounds which can be used as first process step is described, for example, in EP 1 070 695, U.S. Pat. Nos. 6,225,515, 6,015,933 and 6,194,626, in particular U.S. Pat. No. 6,040,489, which are incorporated by reference into the disclosure of the present invention. In this process, a 1,3-butadiene-containing stream is passed together with hydrogen and a solvent into a catalytic extractive distillation unit in which a catalyst which is suitable for the hydrogenation of acetylenically unsaturated compounds is present. Butanes and butenes, which are less readily soluble in the solvent, are distilled off as an overhead stream and removed from the distillation unit. Butadienes and acetylenes, which are more readily soluble in the solvent, are conveyed together with the solvent to the reaction zone present in the catalytic extractive distillation unit. In the reaction zone, the acetylenes are converted into the hydrogenation products. Hydrogenation products which are not butadienes are separated off from the butadienes by the extractive distillation taking place in the unit. The stream comprising the solvent and butadienes is removed as extract stream from the unit and is fed into a stripping column in which the solvent is separated off from the butadiene. Further separation of the butadienes into 1,2- and 1,3-butadiene by distillation can be dispensed with.

As catalysts in this process (U.S. Pat. No. 6,040,489), it is possible to use, in particular the catalysts used in the above-mentioned patents, in particular catalyst compositions comprising copper, one or more metals of transition group VIII of the Periodic Table of the Elements or mixtures thereof and an inorganic oxidic support material. Apart from these materials, further activator metals can be present. Preferred catalysts comprise a composition comprising copper activated with one or more metals from the group consisting of silver, platinum, palladium, manganese, cobalt, nickel, chromium and molybdenum on an aluminum support. Particularly preferred catalysts comprise a composition comprising copper, nickel, manganese and cobalt dispersed on gamma-aluminum oxide, in particular on aluminum oxide having a BET surface area of from 150 to 250 m$^2$/g.

The selective hydrogenation is preferably carried out at a molar ratio of hydrogen to acetylene of from 1 to 5, preferably at a ratio of from 1 to 3, particularly preferably at a ratio of up to 2. The reaction zone in this process is preferably operated at a temperature of from 30 to 100° C., preferably from 32 to 83° C. and particularly preferably from about 50 to about 80° C. The temperature is dependent on the operating pressure, which is preferably from 0.1379 MPa to 1.379 MPa, more preferably from 0.1379 MPa to 3.447 MPa, in the catalytic extractive distillation unit. The temperature at other places in the extractive distillation unit, in particular at the top of the unit, can be up to 150° C. or more.

The solvent is selected so that it has a higher affinity for unsaturated hydrocarbons than for saturated hydrocarbons.

Suitable solvents are, for example, dimethylacetamide, dimethylformamide, furfural, N-methylpyrrolidone, formylmorpholine, hexane and acetonitrile.

The stripping column is preferably operated at a pressure of from about 0.1034 to about 0.3447 MPa and a temperature of from about 30 to about 200° C. The butadienes are obtained as overhead product. The bottom fraction, which comprises the solvent, can be recirculated to the catalytic extractive distillation unit, if appropriate after work-up.

Further details or parameters and process variants of this process used as first process step may be found in U.S. Pat. No. 6,040,489.

Further similar hydrogenation processes and their parameters may be found in EP 1 070 695, U.S. Pat. Nos. 6,225,515, 6,015,933 and 6,194,626, with, in particular, further details regarding the composition of the catalysts being able to be found in U.S. Pat. No. 6,417,419.

It is known that under the hydrogenation conditions indicated the copper catalyst loses activity and has to be regenerated at regular intervals. Various methods of regenerating the catalyst have been described in the literature (U.S. Pat. Nos. 3,912,789, 6,225,515 and 6,194,626); in particular, the alternate use of two reactors is described. The first process step therefore encompasses at least two hydrogenation reactors, so that the overall process can continue to be operated while a catalyst is being regenerated. As described in EP 1 070 695 and U.S. Pat. No. 6,225,515, the regeneration can be carried out by the reactor containing the catalyst which is to be regenerated being brought into contact with hydrogen and a solvent under catalyst regeneration conditions. The temperature is from 32 to 260° C., the pressure is from 1.034 to 3.447 MPa and the LHSV of the solvent is from 0.5 to 10 h$^{-1}$. In addition, the time between successive regenerations can be increased by means of simultaneous metering-in of hydrocarbon stream and solvent during the hydrogenation (EP 1 070 695, U.S. Pat. Nos. 6,271,428 and 6,194,626). To effect regeneration, the catalyst can also be treated at elevated temperature with an oxidant, preferably oxygen, in particular atmospheric oxygen. This regeneration (burning-off) of catalysts is described for copper catalysts in U.S. Pat. Nos. 3,912,789 and 3,897,511 and for palladium catalysts in U.S. Pat. No. 4,551,443.

The first process step can be carried out in one reactor or in a plurality of reactors, with these being able to be connected in series or in parallel. If a plurality of reactors or reactor beds which are operated in parallel, in series or as combinations thereof are used in the first process step of the process of the invention, the hydrogen can be fed in at one or more feed points on each reactor/reactor bed (U.S. Pat. Nos. 4,704,492, 4,126,645, 4,704,492 or 6,417,419). Distribution of the total amount of hydrogen over various feed points can lead to increased selectivity of the hydrogenation. This concept is, for example, subject matter of the document U.S. Pat. No. 4,704,492, which is incorporated by reference into the disclosure of the present invention.

Hydrogen which has not been reacted in the first process step can be separated off in its entirety or partly by known methods after this step or can be fed together with the $C_4$-hydrocarbons to the second process step. The hydrogen can be separated off, for example, in a degassing vessel or as offgas stream in a distillation.

To keep the losses of 1,3- and 1,2-butadiene very small, the acetylenically unsaturated compounds are preferably not hydrogenated completely. For this reason, the hydrocarbon streams obtained from the first process step preferably contain from 0 to 1 ppm by mass, preferably at least 0.1 ppm by mass and particularly preferably at lest 0.5 ppm by mass of acetylenically unsaturated compounds. The degree of hydrogenation can be set by means of appropriate selection of the process parameters, e.g. choice of the catalyst, residence time of the reaction mixture in the reactor, reaction temperature and amount and/or pressure of the hydrogen used, with the appropriate parameters being able to be determined by means of simple preliminary tests.

The content of allenically unsaturated compounds (e.g. 1,2-butadiene) in the hydrocarbon stream obtained from the first process step can, depending on the starting material, be, for example, in the range from 0.05 to 2% by mass. The content of allenically unsaturated compounds (e.g. 1,2-butadiene) in the hydrocarbon stream obtained from the first process step is preferably at least 80% (relative), more preferably at least 85% (relative), particularly preferably at least 90% (relative) and very particularly preferably at least 95% (relative), of the original content of allenically unsaturated compounds The 1,3-butadiene content is, depending on the concentration in the starting hydrocarbon stream, in the region of the inlet concentration. As a result of hydrogenation of butenine to 1,3-butadiene, the 1,3-butadiene content can increase by an amount corresponding to the amount of butenine present. At the same time, a small part of the 1,3-butadiene can be lost as a result of hydrogenation or be reacted in secondary reactions, for example to form high boilers (green oil). In the process claimed, the butadiene content after the first process step is preferably in the range from a maximum of 10% (absolute) above to a minimum of 10% (absolute) below the inlet concentration of 1,3-butadiene in the first process step, preferably in the range from 5% (absolute) above to 5% (absolute) below the inlet concentration of 1,3-butadiene.

The output from the hydrogenation can contain a small amount of high boilers (green oil) which have been formed during the hydrogenation. It can be advantageous to separate off the high boilers from the hydrocarbon stream obtained as hydrogenation product from the first process step before it is fed to the second process step (telomerization). The high boilers can comprise, for example, compounds having more than 4 or 5 carbon atoms, with the compounds (green oil) formed during the process mostly having more than 5 carbon atoms. Components having 5 carbon atoms are mostly introduced into the process as impurities in the raw material, but can, as a matter of choice, be separated off together with the green oil or can remain in their entirety or partly in the $C_4$ stream. The high boilers can be separated off prior to the telomerization, for example by distillation. The output from the hydrogenation, i.e. the process product from the first process step, is preferably used directly, i.e. without removal of the high boiler, as starting material in the second process step (telomerization).

1,3-Butadiene streams from other sources can optionally be mixed with the output from the first process step and this mixture can be used in the telomerization, with the concentration of acetylenically unsaturated compounds in the total stream fed to the telomerization being less than or equal to 100 ppm. These can be, for example, streams which are obtained in a butadiene plant in which 1,3-butadiene is isolated by extractive distillation.

As indicated above, the hydrocarbon mixture which is fed to the telomerization step preferably has a content of acetylenically unsaturated compounds of less than or equal to 50 ppm by mass, particularly preferably 20 ppm by mass.

The nucleophiles used in the telomerization step of the process of the invention in addition to the hydrocarbon stream from the first process step are preferably compounds of the formulae III, IV and V

where $R^a$ and $R^{1b}$ are selected independently from among hydrogen, a linear, branched or cyclic $C_1$-$C_{22}$-alkyl group, an alkenyl group, an alkenyl group, a $C_5$-$C_{18}$-aryl group or a —CO-alkyl-($C_1$-$C_8$) group or a —CO-aryl-($C_5$-$C_{10}$) group, with these groups being able to contain substituents selected from the group consisting of —CN, —COOH, —COO-alkyl-($C_1$-$C_8$), —CO-alkyl-($C_1$-$C_8$), -aryl-($C_5$-$C_{10}$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), 13 CHO, —SO$_3$H, —NH$_2$, —F, —Cl, —OH, —CF$_3$, —NO$_2$, and the radicals $R^{1a}$ and $R^{1b}$ can be joined to one another via covalent bonds. Particularly preferred nucleophiles are compounds in which the radicals $R^{1a}$ and $R^{1b}$ are each hydrogen, methyl, ethyl, n-propyl, isopropyl, tert-butyl, n-butyl, sec-butyl, pentyl, hexyl, heptyl octyl, octenyl, octadienyl, isononyl, 2-ethylhexyl, n-nonyl, phenyl, m-, o- or p-methylphenyl, naphthyl, 2,4-di-ter-butylphenyl, 2,6-di-tert-butylmethylphenyl, hydrogencarbonyl, methylcarbonyl, ethylcarbonyl, propylcarbonyl or phenylcarbonyl.

Specifically, these are
water, ammonia,
monoalcohols and phenols such as methanol, ethanol, n-propanol, isopropanol, allyl alcohol, n-butanol, i-butanol, octanol, 2-ethylhexanol, isononanol, benzyl alcohol. cyclohexanol, cyclopentanol or 2,7-octadien-1-ol, phenol,
dialcohols such as ethylene glycol, 1,2-propanediol, 1,3-propanediol, 1,4-butanediol, 1,2-butanediol, 2,3-butanediol and 1,3-butanediol,
hydroxy compounds such as α-hydroxyacetic esters,
primary amines such as methylamine, ethylamine, propylamine, butylamine, octylamine, 2,7-octadienylamine, dodecylamine, ethylenediamine or hexamethylenediamine,
secondary amines such as dimethylamine, diethylamine, N-methylaniline, bis(2,7-octadienyl amine, dicyclohexylamine, methylcyclohexylamine, pyrrolidine, piperidine, morpholine, piperazine or hexamethylenimine or
carboxylic acids such as formic acid, acetic acid, propanoic acid, butenoic acid, isobutenoic acid, benzoic acid, 1,2-benzenedicarboxylic acid (phthalic acid).

Very particularly preferred compounds for use as nucleophiles in the telomerization step are methanol, ethanol, 2-ethylhexanol, octanol, octenol, octadienol, isopropanol, n-propanol, isobutanol, n-butanol, isononanol, formic acid, acetic acid, propionic acid, n-butanoic acid, isobutanoic acid, benzoic acid, phthalic acid, phenol, dimethylamine, methylamine, ammonia and/or water. Methanol is advantageously used as nucleophile.

Nucleophiles which can themselves be obtained via a telomerization reaction can be introduced directly or else be formed in situ. Thus, for example, 2,7-octadien-1-ol can be formed in situ from water and butadiene in the presence of the telomerization catalyst, 2,7-octadienylamine can be formed from ammonia and 1,3-butadiene, etc.

In deciding the ratio of nucleophile to 1,3-butadiene in the telomerization reaction, the number of active hydrogen atoms in the telogen has to be taken into account. Thus, for example, methanol has one active hydrogen atom, ethylene glycol has two, methylamine has two, etc.

Preference is given to using from 0.001 mol to 10 mol of 1,3-butadiene in the telomerization reaction per mole of active hydrogen atoms of the nucleophile which can react with the 1,3-butadiene. Wen the reaction is carried out in the liquid phase, a ratio of from 0.1 mol to 2 mol of 1,3-butadiene per mole of active hydrogen is particularly preferred.

Catalysts used for the telomerization are complexes, in particular carbene complexes, of the metals palladium (Pd), iron (Fe), ruthenium (Ru), osmium (Os), cobalt (Co), rhodium (Rh), iridium (Ir), nickel (Ni) or platinum (Pt). Preference is given to using palladium compounds, in particular palladium-carbene complexes as catalyst in the telomerization step.

The ligands in the metal complexes used as catalyst are, for example, trivalent phosphorus compounds or carbenes. Metal complexes having at least one heteroatom-stabilized carbene as ligand are preferably used as catalyst. Examples of such ligands are described, inter alia, in the documents DE 101 28 144, DE 101 49 348, DE 101 48 722, DE 100 62 577, EP 1 308 157 and WO 01/66248. These documents and, in particular, the ligands described there are incorporated by reference in the disclosure of the present patent application. Furthermore, the active complex can bear further ligands.

Suitable carbene ligands are, in particular, compounds having the structural formulae VI to IX:

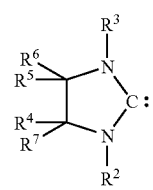

VI

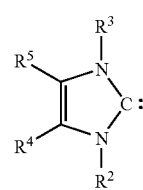

VII

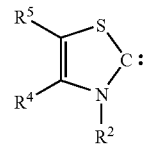

VIII

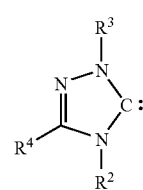

IX

In the structural formulae VI to IX, the radicals $R^2$ to $R^7$ have the following meanings:

R$^2$; R$^3$: identical or different, a) linear, branched, substituted or unsubstituted cyclic or alicyclic alkyl groups having from 1 to 24 carbon atoms,
  or b) substituted or unsubstituted, monocyclic or polycyclic aryl groups having from 6 to 24 carbon atoms.
  or c) monocyclic or polycyclic, substituted or unsubstituted heterocycles having from 4 to 24 carbon atoms and at least one heteroatom from the group consisting of N, O, S;
R$^4$, R$^5$, R$^6$, R$^7$: identical or different,
  hydrogen, alkyl, aryl, heteroaryl, —CN, —COOH, —COO-alkyl-, —COO-aryl-, —OCO-alkyl-, —OCO-aryl-, —OCOO-alkyl-, —OCOO-aryl-, —CHO, —CO-alkyl-, —CO-aryl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferrocenyl, —SO$_3$H, —PO$_3$H$_2$, where the alkyl groups have 1-24 carbon atoms and the aryl and heteroaryl groups have from 5 to 24 carbon atoms and the radicals R$^4$ and R$^5$ may also be part of a bridging aliphatic or aromatic ring.

In particular, R$^2$ and R$^3$ are
linear branched, cyclic or alicyclic alkyl groups having from 1 to 24 carbon atoms,
monocyclic or polycyclic aryl groups having from 6 to 24 carbon atoms or
monocyclic or polycyclic rings containing at least one heteroatom selected from among the elements nitrogen, oxygen and sulfur, any further substituents are selected from among the groups —CN, —COOH, —COO-alkyl-, —COO-aryl-, —OCO-alkyl-, —OCO-aryl-, —OCOO-alkyl-, —OCOO-aryl-, —CHO, —CO-alkyl-, —CO-aryl-, -aryl-, -alkyl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferrocenyl, —SO$_3$H, —PO$_3$H$_2$. The alkyl groups of the substituents have from 1 to 24 carbon atoms and the aryl groups of the substituents have from 5 to 24 carbon atoms.

The radicals R$^4$, R$^5$, R$^6$ and/or R$^7$ can be identical or different and can bear at least one substituent from the group consisting of —H, —CN, —COOH, —COO-alkyl, —COO-aryl, —OCO-alkyl, —OCO-aryl, —OCOO-alkyl, —OCOO-aryl, —CHO, —CO-alkyl, —CO-aryl, -aryl, -alkyl, -alkenyl, -allyl, —O-alkyl, —O-aryl, —NH$_2$, —NH(alkyl), —N(alkyl)$_2$, —NH(aryl), —N(alkyl)$_2$, —F, —Cl, —Br, —I, —OH, —CF$_3$, —NO$_2$, -ferrocenyl, —SO$_3$H, —PO$_3$H$_2$, where the alkyl groups can have from 1 to 24 carbon atoms, preferably from 1 to 20 carbon atoms, the alkenyl groups can have from 2 to 24 carbon atoms, the allyl groups can have from 3 to 24 carbon atoms and the monocyclic or polycyclic aryl groups can have from 5 to 24 carbon atoms.

The radicals R$^4$ to R$^6$ can be covalently joined to one another via, for example, CH$_2$— or CH— groups.

Substituents having acidic hydrogen atoms can also have metal or ammonium ions in place of the protons.

The radicals R$^2$ and R$^3$ are, inter alia, monocyclic or polycyclic rings containing at least one heteroatom. These are, for example, radicals derived from 5- and 6-membered heteroalkanes, heteroalkenes and heteroaromatics such as 1,4-dioxane, morpholine, γ-pyran, pyridine, pyrimidine, pyrazine, pyrrole, furan, thiophene, pyrazole, imidazole, thiazole and oxazole. Specific examples of such radicals R$^2$ and R$^3$ are shown in the table below. In these radicals~in each case indicates the point of linkage to the five-membered heterocycle.

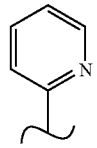

A-1

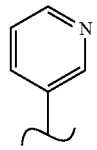

A-2

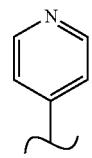

A-3

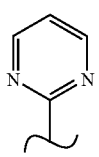

A-19

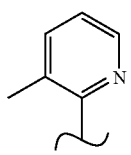

A-4

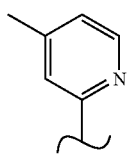

A-5

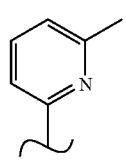

A-6

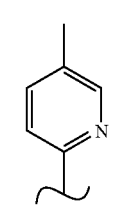

-continued

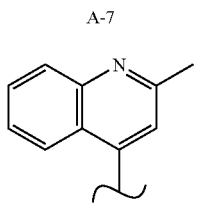
A-7

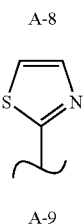
A-8

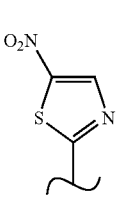
A-9

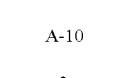
A-10

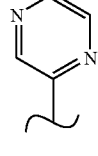
A-11

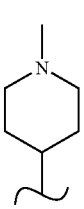
A-12

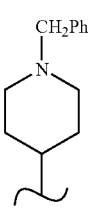
A-13

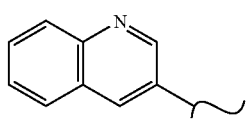
A-14

-continued

A-15

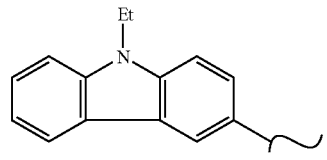
A-16

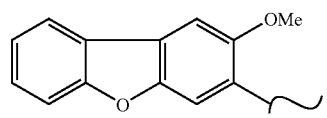
A-17

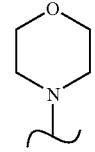
A-18

The radicals $R^2$ and $R^3$ are particularly preferably substituted or unsubstituted phenyl radicals, for example, 2,4,6-trimethylphenyl or 2,6-diisopropylphenyl. Particular preference is given to the radicals $R^4$, $R^5$, $R^6$ and $R^7$ being hydrogen, methyl, F or Cl.

The metal-carbene complexes can be used as such in the telomerization reaction or can be generated in situ during this reaction. In the preparation of the catalyst in the reaction mixture, it is usual to react a quaternary ammonium salt having an appropriate structure with a base to form the carbene of which at least a proportion coordinates to the metal present in the solution.

As solvent for the telomerization reaction, the nucleophile used is generally employed if it is present as a liquid under the reaction conditions. However, other solvents can also be used. The solvents used should be largely inert. Solvents are preferably added when nucleophiles which are present as solids under the reaction conditions are used or when products which are solids under the reaction conditions would be obtained. Suitable solvents are, inter alia, aliphatic, cycloaliphatic and aromatic hydrocarbons such as $C_3$-$C_{20}$-alkanes, mixtures of lower alkanes ($C_3$-$C_{20}$) cyclohexane, cyclooctane, ethylcyclohexane, alkenes and polyenes, vinylcyclohexene, 1,3,7-octatriene, the $C_4$-hydrocarbons from $C_4$ fractions from a cracker, benzene, toluene and xylene; polar solvents such as tertiary and secondary alcohols, amides such as acetamide, dimethylacetamide and dimethylformamide, nitriles such as acetonitrile and benzonitrile, ketones such as acetone, methyl isobutyl ketone and diethyl ketone; carboxylic esters such as ethyl acetate, ethers such as dipropyl ether, diethyl ether, dimethyl ether, methyl octyl ether, methyl tert-butyl ether, ethyl tert-butyl ether 3-methoxyoctane, dioxane, tetrahydrofuran, anisole, alkyl and aryl ethers of ethylene glycol, diethylene glycol, triethylene glycol, tetraethylene glycol, polyethylene glycol, propylene glycol, dipropylene glycol, tripropylene glycol and polypropylene glycol and other polar solvents such as sulfolane, dimethyl sulfoxide, ethylene carbonate, propylene carbonate and water. Ionic liquids, for example imidazolium, or pyridinium salts, can also be used as solvents. The solvents can be used either alone or as mixtures of various solvents.

The temperature at which the telomerization reaction is carried out is preferably in the range from 10 to 180° C., more preferably in the range from 30 to 120° C. and particularly preferably in the range from 40 to 100° C. The reaction pressure is preferably from 1 to 300 bar, more preferably from 1 to 120 bar, particularly preferably from 1 to 64 bar and very particularly preferably from 1 to 20 bar, The concentration of the catalyst, formally reported in ppm (mass) of catalyst metal based on the total mass, is from 0.01 ppm to 1000 ppm, preferably from 0.5 to 100 ppm, particularly preferably from 1 to 50 ppm.

The ratio [mol/mol] of carbene to metal is preferably from 0.01:1 to 250:1, preferably from 1:1 to 100:1 and particularly preferably from 1:1 to 50:1. Apart from carbene ligands, further ligands, for example phosphorus ligands such as triphenylphosphine, can also be present in the reaction mixture.

It is often advantageous to carry out the telomerization reaction in the presence of bases. Preference is given to using basic components having a $pK_b$ of less than 7, in particular compounds selected from the group consisting of amines, alkoxides, phenoxides, alkali metal salts, alkaline earth metal salts.

Suitable basic components are, for example, amines such as trialkylamines which may be alicyclic or/and open-chained, amides, alkali metal or/and alkaline earth metal salts of aliphatic or/and aromatic carboxylic acids, e.g. acetates, propionates, benzoates or appropriate carbonates, hydrogencarbonates, alkoxides of alkali metals and/or alkaline earth metals, phosphates, hydrogenphosphates or/and hydroxides, preferably of lithium, sodium, potassium, calcium, magnesium, cesium, ammonium compounds and phosphonium compounds. Preference is given to hydroxides of the alkali metals and alkaline earth metals and metal salts of the nucleophile of the general formula III, IV or V as additive.

The basic component is preferably used in an amount of from 0.01 mol % to 10 mol % (based on the olefin), preferably from 0.1 mol % to 5 mol % and very particularly preferably from 0.2 mol % to 1 mol %.

The telomerization can be operated continuously or batchwise and is not restricted to the use of particular types of reactor. Examples of reactors in which the reaction can be carried out are stirred tank reactors, cascades of stirred tanks, flow tubes and loop reactors. It is also possible to use combinations of various reactors, for example a stirred tank reactor with a downstream flow tube.

The telomerization is, in order to obtain a high space-time yield, not carried out to complete conversion of the 1,3-butadiene. It is advantageous to restrict the conversion to a maximum of 95%, preferably 88%.

The output from the second process step can, for example, comprise mainly the telomerization product, by-products, "inert $C_4$-hydrocarbons", residual amounts of 1,3-butadiene, residual amounts of nucleophile and catalyst system (catalyst metal, ligands, bases, etc.) or further reaction products thereof and any added solvents. The 1,2-butadiene is also present in this product mixture.

The allenes present in the output from the telomerization, in particular the 1,2-butadiene, can be separated off from the telomerization product mixture by, for example, distillation.

The fractionation of the output from the second process step can also be carried out quite generally by known industrial methods such as distillation or extraction. For example, separation into the following fractions by distillation can be carried out:

a $C_4$ fraction comprising n-butane, isobutane, 1-butene, 2-butenes, isobutene, 1,3-butadiene, 1,2-butadiene and possibly all or some of the nucleophile, a fraction comprising the target product (2,7-octadienyl derivative), a fraction comprising the by-product and/or a fraction comprising the catalyst and if appropriate a fraction comprising the nucleophile and/or if appropriate a solvent fraction The fraction comprising the nucleophile, the fraction comprising the solvent and the fraction comprising the catalyst can in each case be recirculated in its entirety or partly to the second process step or else be passed to a work-up.

The target product of the formula I is utilized as such or serves as precursor for other materials. For example, the target product 1-methoxyoctadi-2,7-ene can be converted by hydrogenation of the two double bonds and subsequent elimination of methanol into 1-octene.

In a preferred embodiment, the process comprises a third process step in which the $C_4$ fraction is separated of from the remaining output from the second process step. The $C_4$-hydrocarbon fraction obtained in the separation can still contain part of the nucleophile, particularly when azeotropes are formed between the nucleophile and one or more of the $C_4$ components. Examples of nucleophiles which form such azeotropes are water and methanol.

The $C_4$ fraction can be worked up in various ways. One way is firstly to separate off the 1,2-butadiene from the $C_4$ fraction, e.g. by means of distillation and/or extractive distillation, and pass it to a further use. As an alternative, the $C_4$ fraction can be fed to a selective hydrogenation in which the dienes are removed, i.e. residual 1,3-butadiene and the 1,2-butadiene are converted into 1-butene and 2-butenes. Such hydrogenations are known from the prior art and are described, for example, in U.S. Pat. No. 5,475,173, DE 3119850 and F. Nierlich, F. Obenhaus, Erdöl & Kohle, Erdgas, Petrochemie (1986) 39, 73-78. Industrially, they are carried out both in a single stage and in a plurality of stages. The hydrogenation in the liquid phase is preferably carried out over heterogeneous supported palladium catalysts. Any nucleophile present in the $C_4$ fraction can, if necessary, be separated off by known methods before or after the hydrogenation. Nucleophiles which are readily soluble in water (for example methanol) can, for example, be removed by means of a water scrub. To dry the $C_4$ stream, drying columns, inter alia, have been found to be useful. The resulting mixture of $C_4$-hydrocarbons which is largely free of 1,3-butadiene, 1,2-butadiene and nucleophile (butadiene content preferably less than 5000 ppm) corresponds very largely to commercial raffinate I and can be processed further or worked up like raffinate I in known processes. For example, it can be used for preparing tert-butyl alcohol, diisobutene (or isooctane), methyl tert-butyl ether, ethyl tert-butyl ether, 1-butene or $C_4$ dimers and oligomers.

If methanol or ethanol is used as nucleophile in the second process step, one has the option of not removing the nucleophile but instead passing the output from the hydrogenation directly to an etherification in which the alcohol is reacted with the isobutene present in the $C_4$ stream to form methyl tert-butyl ether or ethyl tert-butyl ether. This reaction, too, is carried out by processes known in industry, usually in the presence of ion exchangers as catalysts. To achieve complete conversion of the isobutene, additional alcohol may have to be added.

The following examples illustrate the invention without restricting its scope which is defined by the description and the claims.

EXAMPLE 1

Selective Hydrogenation Using a Copper-Containing Catalyst

The hydrogenation plant comprised a flooded trickle-bed reactor having a diameter of 14 mm and a length of 2 m and was provided with an external circuit. The reactor was heated electrically so that the reaction could be carried out adiabatically. The volume of the catalyst was 0.307 l. As catalyst, use was made of a copper-zinc catalyst: 6% of Cu on ZnO pellets of the type H9016 from Degussa. The inlet temperature was 30° C., and the pressure in the reactor was brought to 10 bar by means of hydrogen. The total amount of $C_4$-hydrocarbon mixture fed in was 1.853 kg. The selective hydrogenation was carried out using a method based on GB 1,066,765. The composition of the product from the selective hydrogenation is shown in Table 1. It can clearly be seen that the content of vinylacetylene and 1-butyne has been reduced to zero after four hours of operation, without the content of 1,3-butadiene and of 1,2-butadiene having changed significantly.

EXAMPLE 2

Telomerization of 1,3-butadiene-Containing $C_4$-hydrocarbon Mixtures with methanol General Method for the Telomerization In a 100 ml Schlenk tube, 55.9 mg (0.18mmol) of palladium acetylacetonate and 0.393 g (0.75 mmol) of 1,3-bis(2,4,6-trimethylphenyl)imidazolium-o-cresoxide-o-cresol were dissolved in 50 g (1.56 mol) of methanol under protective gas. In a 3-liter autoclave from Büchi, 6.72 g (0.06 mol) of o-cresol (heated to 40° C. on a water bath) and 3.47 g (0.06 mol) of sodium methoxide were dissolved in 115 g (3.59 mol) of methanol and in 100 g (0.52 mol) of tripropylene glycol. 550 g of a $C_4$-hydrocarbon mixture were subsequently injected into the autoclave by means of a gas pressure can (amount determined by decreasing mass in the $C_4$ stock bottle). The autoclave was heated to the reaction temperature while stirring, the palladium-containing solution was added to the contents of the autoclave and the reaction was monitored by means of an online gas chromatograph. The reaction time was 14 hours.

GC Analysis:

GC (1st column: DB-WAX/$Al_2O_3$, 2nd column: DB-Wax/HP-5MS; initial temperature: 50° C., maximum temperature: 200° C., start time: 1 min equilibration time: 3 min; temperature program: from 50° C. at 15° C. $min^{-1}$ to 200° C., running time: 11 min; irj.: 220° C., const. flow).

$t_R$(C4-hydrocarbons)=2.762 min.

$t_R$(methanol)=3.152 min, $t_R$(1,7-octadiene)=3.866 min, $t_R$(trans-1,6-octadiene)=3.958 min, $t_R$(cis-1,6-octadiene)=4.030 min, $t_R$(cis-1,3,7-octatriene)=4.291 min. $t_R$(trans-1,3,7-octatriene)=4.292 min, $t_R$(vinylcyclohexene)=4.448 min, $t_R$(i-butane)=4.552 min, $t_R$(n-butane)=4.822 min, $t_R$(3-MODE)=5.523 min, $t_R$(trans-butene)=6.116 min, $t_R$(1-butene)=6.240 min, $t_R$(i-butene)=6.412 min, $t_R$(cis-butene)=6.616 min, $t_R$(1-MODE)=6.650 min, $t_R$(1,2-butadiene)=6.900 min, $t_R$(1,3-butadiene)=7.526 min.

2,7-octadienyl 1-methyl ether(=1-MODE)

1,7-octadienyl 3-methyl ether(=3-MODE)

EXAMPLE 2.1

In the example according to the invention, the $C_4$-hydrocarbon mixture from Example 1 was used.

EXAMPLE 2.2

In the example according to the invention, an acetylene-free and allene-containing $C_4$-hydrocarbon mixture comprising 43.53% by weight of 1,3-butadiene, 1.95% by weight of i-butane, 4.79% by weight of n-butane, 4.58% by weight of trans-butene, 17.20% by weight of 1-butene, 24.55% by weight of i-butene, 3.15% by weight of cis-butene, 0.1% by weight of 1,2-butadiene was used.

COMPARATIVE EXAMPLE 2.3

In the comparative example, an acetylene-free and allene-free $C_4$-hydrocarbon mixture comprising 43.19% by weight of 1,3-butadiene, 1.73% by weight of i-butane, 6.86% by weight of n-butane, 5.12% by weight of trans-butene, 14.80% by weight of 1-butene, 24.56% by weight of i-butene, 3.57% by weight of cis-butene is used.

COMPARATIVE EXAMPLE 2.4

In the comparative example, an acetylene-containing and allene-free $C_4$-hydrocarbon mixture comprising 43.19% by weight of 1,3-butadiene, 1.73% by weight of i-butane, 6.86% by weight of n-butane, 5.12% by weight of trans-butene, 14.80% by weight of 1-butene, 24.56% by weight of i-butene, 3.57% by weight of cis-butene, 0,0015% by weight of vinylacetylene and 0.0012% by weight of 1-butyne was used.

COMPARATIVE EXAMPLE 2.5

In this comparative example, an acetylene-containing and allene-containing $C_4$-hydrocarbon mixture comprising 43.53% by weight of 1,3-butadiene, 1.95% by weight of i-butane, 4.79% by weight of n-butane, 4.58% by weight of trans-butene, 17.20% by weight of 1-butene, 24.55% by weight of i-butene, 3.15% by weight of cis-butene, 0.11% by weight of 1,2-butadiene. 0.0017% by weight of vinylacetylene and 0.0010% by weight of 1-butyne was used.

The results of Examples 2.1 to 2.5 may be found in Table 2. Comparative example 2.3 shows that allenes have no influence on the catalysis performance. Comparative examples 2.4 and 2.5 likewise show that allenes have no influence on the catalysis. Although the catalysis starts somewhat more slowly, 100% conversions are nevertheless achieved at equally high selectivities.

TABLE 1

Result of the selective hydrogenation of $C_4$-hydrocarbon mixtures

| Time [h] | i-Butane [% by wt.] | n-Butane [% by wt.] | trans-Butene [% by wt.] | 1-Butene [% by wt.] | i-Butene [% by wt.] | cis-Butene [% by wt.] | 1,2-Butadiene [% by wt.] | 1,3-Butadiene [% by wt.] | Vinylacetylene [% by wt.] | 1-Butyne [% by wt.] | Remainder [% by wt.] |
|---|---|---|---|---|---|---|---|---|---|---|---|
| 0.00 | 3.82 | 6.67 | 3.90 | 14.80 | 24.01 | 2.55 | 0.12 | 43.25 | 0.74 | 0.13 | 0.01 |
| 0.25 | 3.81 | 6.52 | 4.03 | 14.81 | 24.02 | 2.59 | 0.12 | 43.33 | 0.62 | 0.12 | 0.04 |
| 0.50 | 3.80 | 6.52 | 4.00 | 14.85 | 23.94 | 2.62 | 0.10 | 43.45 | 0.57 | 0.13 | 0.02 |
| 0.75 | 3.81 | 6.49 | 4.01 | 14.82 | 23.97 | 2.64 | 0.12 | 43.44 | 0.55 | 0.13 | 0.03 |
| 1.00 | 3.78 | 6.51 | 4.05 | 14.88 | 23.97 | 2.60 | 0.14 | 43.41 | 0.52 | 0.12 | 0.04 |
| 1.50 | 3.79 | 6.54 | 4.13 | 15.06 | 24.03 | 2.66 | 0.10 | 43.23 | 0.35 | 0.11 | 0.02 |
| 2.25 | 3.82 | 6.53 | 4.16 | 15.23 | 24.15 | 2.68 | 0.14 | 42.99 | 0.19 | 0.09 | 0.03 |
| 2.50 | 3.82 | 6.52 | 4.16 | 15.32 | 24.01 | 2.64 | 0.14 | 43.14 | 0.12 | 0.11 | 0.03 |
| 3.00 | 3.83 | 6.56 | 4.25 | 15.50 | 24.17 | 2.71 | 0.12 | 42.69 | 0.08 | 0.07 | 0.04 |
| 3.50 | 3.80 | 6.53 | 4.35 | 15.62 | 24.04 | 2.73 | 0.13 | 42.73 | 0.00 | 0.06 | 0.02 |
| 4.00 | 3.85 | 6.53 | 4.43 | 15.96 | 24.21 | 2.70 | 0.11 | 42.19 | 0.00 | 0.00 | 0.02 |
| 4.50 | 3.83 | 6.57 | 4.59 | 16.34 | 24.10 | 2.74 | 0.11 | 41.68 | 0.00 | 0.00 | 0.04 |

TABLE 2

Result of the telomerization (Example 2)

| Example 2.1 | | | Example 2.2 | | | Comparative example 2.3 | | | Comparative example 2.4 | | | Comparative example 2.5 | | |
|---|---|---|---|---|---|---|---|---|---|---|---|---|---|---|
| Time [min] | Conversion [%] | Selectivity [%] | Time [min] | Conversion [%] | Selectivity [%] | Time [min] | Conversion [%] | Selectivity [%] | Time [min] | Conversion [%] | Selectivity [%] | Time [min] | Conversion [%] | Selectivity [%] |
| 0 | 1.9 | 90.1 | 0 | 2.6 | 100.0 | 0 | 0.0 | 0.0 | 0 | 1.5 | 88.8 | 0 | 3.6 | 100 |
| 140 | 68.4 | 96.6 | 140 | 73.0 | 96.8 | 140 | 65.6 | 96.7 | 138 | 32.5 | 96.4 | 140 | 55.7 | 97.0 |
| 360 | 100.0 | 96.6 | 340 | 100.0 | 96.9 | 830 | 100.0 | 95.9 | 540 | 100.0 | 96.6 | 420 | 100.0 | 96.8 |
| 780 | 100.0 | 96.0 | 820 | 100.0 | 96.3 | 950 | 99.9 | 95.9 | 840 | 100.0 | 96.3 | 840 | 100.0 | 96.1 |

Conversion = conversion of 1,3-butadiene,
selectivity = selectivity to 1-MODE

The invention claimed is:

1. A process for preparing a compound of the formula I

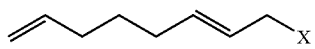

in which X is an $OR^{1a}$ or $NR^{1a}R^{1b}$ radical, where $R^{1a}$ and $R^{1b}$ are selected independently from among hydrogen, a linear, branched or cyclic $C_1$-$C_{22}$-alkyl group, an alkenyl group, an alkynyl group, a $C_5$-$C_{18}$-aryl group or a —CO-alkyl-($C_1$-$C_8$) group or a —CO-aryl-($C_5$-$C_{10}$) group, with these groups being able to contain substituents selected or the group consisting of —CN, —COOH, —COO-alkyl-($C_1$-$C_8$), —CO-alkyl-($C_1$-$C_8$), -aryl-($C_5$-$C_{10}$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1C_8$), —CHO, —SO$_3$H, —NH$_2$, —F, —Cl, —OH, —CF$_3$, —NO$_2$ and the radicals $R^{1a}$ and $R^{1b}$ being able to be joined to one another via covalent bonds, from a 1,3-butadiene-containing hydrocarbon stream comprising allenically unsaturated compounds and more than 100 ppm by mass of acetylenically unsaturated compounds, in which process the acetylenically unsaturated compounds are removed in a first process step and 1,3-butadiene is reacted with a nucleophile in the presence of a metal compound in a second process step (telomerization step), wherein the hydrocarbon stream which is obtained from the first process step and is used as starting material in the second process step has a content of acetylenically unsaturated compounds of less than or equal to 100 ppm by mass and a content of allenically unsaturated compounds which is at least 75% (relative) of the original content of allenically unsaturated compounds.

2. The process as claimed in claim 1, wherein a compound of the formula IIA or IIB,

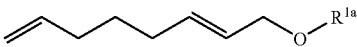

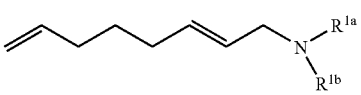

is prepared by reacting 1,3-butadiene with a nucleophile of the formula III, IV or V

where $R^{1a}$ and $R^{1b}$ are as defined in claim 1.

3. The process as claimed in claim 1, wherein a $C_4$-hydrocarbon fraction is used as hydrocarbon stream.

4. The process as claimed in claim 1, wherein the acetylenically unsaturated compounds are separated by extraction.

5. The process as claimed in claim 1, wherein acetylenically unsaturated compounds are removed by hydrogenation.

6. The process as claimed in claim 5, wherein a copper-containing catalyst is used in the hydrogenation.

7. The process as claimed in claim 5, wherein a palladium-containing catalyst is used in the hydrogenation.

8. The process as claimed in claim 5, wherein compounds having more than 4 or 5 carbon atoms are separated from the hydrocarbon stream obtained as hydrogenation product mixture from the first process step before it is fed to the second process step (telomerization).

9. The process as claimed in claim 1, wherein the hydrocarbon stream obtained as process product from the first process step is used directly as starting material in the second process step.

10. The process as claimed in claim 1, wherein the hydrocarbon stream obtained as process product from the first process step is mixed with a 1,3-butadiene stream from a butadiene plant and this mixture is used in the second process step.

11. The process as claimed in claim 1, wherein the content of acetylenically unsaturated compounds in the hydrocarbon mixture which is fed to the telomerization step is less than 50 ppm by mass.

12. The process as claimed in claim 11, wherein the content of acetylenically unsaturated compounds in the hydrocarbon mixture which is fed to the telomerization step is less than 20 ppm by mass.

13. The process as claimed in claim 1, wherein the nucleophile used in the second process step is methanol, ethanol, 2-ethylhexanol, octanol, octenol, octadienol, isopropanol, n-propanol, isobutanol, n-butanol, isononanol, formic acid, acetic acid, propionic acid, n-butanoic acid, iso-butanoic acid, benzoic acid, phthalic acid, phenol, dimethylamine, methylamine, ammonia or water.

14. The process as claimed in claim 1, wherein a metal-carbene complex is used as telomerization catalyst in the second process step.

15. The process as claimed in claim 14, wherein a palladium-carbene complex is used as telomerization catalyst n the second process step.

16. The process as claimed in claim 1, wherein the allenically unsaturated compounds are separated from the telomerization product mixture by distillation.

17. The process as claimed in claim 1, wherein a $C_4$ fraction is separated from the output from the second process step and dienes are removed from the treated output by selective hydrogenation.

18. The process as claimed in claim 17, wherein the hydrogenated $C_4$ fraction is worked-up like raffinate I.

19. The process as claimed in claim 1, wherein X in the formula I is $OR^{1a}$ or $NR^{1a}R^{1b}$, where $R^{1a}$ H, methyl, ethyl, n-propyl, isopropyl, tert-butyl, n-butyl, sec-butyl, pentyl, hexyl, heptyl, octyl, octenyl, octadienyl, isononyl, 2-ethylhexyl, n-nonyl, phenyl, m-, o- or p-methylphenyl, naphthyl, 2,4-di-tert-butylphenyl, 2,6-di-ter-butylmethylphenyl, hydrogencarbonyl, methyl-carbonyl, ethylcarbonyl, propylcarbonyl or phenylcarbonyl and $R^{1b}$ is H, methyl, ethyl, n-propyl, isopropyl, tert-butyl, n-butyl, sec-butyl, pentyl, hexyl, heptyl, octyl, octenyl, octadienyl, isononyl, 2-ethylhexyl, n-nonyl, phenyl, m-, o- or p-methylphenyl, naphthyl, 2,4-di-tert-butylphenyl, 2,6-di-tert-butylmethylphenyl, hydrogencarbonyl, methyl-carbonyl, ethylcarbonyl, propylcarbonyl or phenylcarbonyl.

* * * * *